June 23, 1970 H. KERRIGAN Plant Pat. 2,971
AZALEA PLANT
Filed June 3, 1968
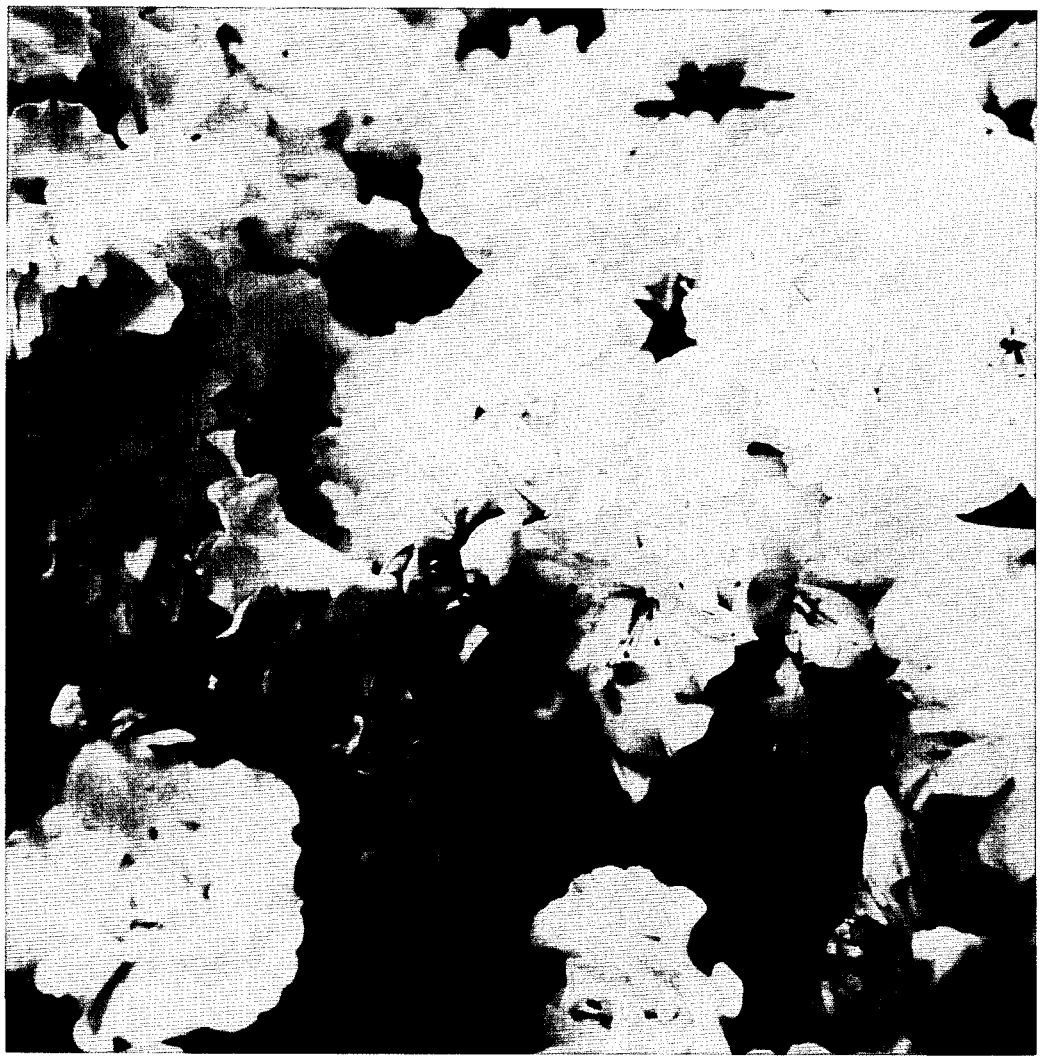

United States Patent Office

Plant Pat. 2,971
Patented June 23, 1970

2,971
AZALEA PLANT

Howard Kerrigan, 3003 Totterdell St.,
Oakland, Calif. 94611

Filed June 3, 1968, Ser. No. 734,177
Int. Cl. A01h 5/02
U.S. Cl. Plt.—55 1 Claim The invention relates to a new and distinct variety of azalea plant of the Belgian-Indica type, originated by me in 1948 as a consequence of the breeding program begun in 1943. The parentage of my new azalea plant is as follows:

Blushing Bride (unpatented) × Snowdrift (unpatented).

The object of the cross was to produce a plant with double white flowers which would bloom after the Belgian-Indica season was over.

These objectives were achieved along with other desirable improvements, as evidenced by the following unique combination of characteristics which are outstanding in the new variety and which distinguish it from its parents as well as from all other varieties of which I am aware. My new variety is primarily characterized by:

A normal flowering date substantially later than mos' Belgian-Indicas, reaching peak bloom about the second or third week in May; by its nearly pure white, double blooms; by its long blooming period and exceptional retention of bloom; and by its vigor; ease of propagation and compact habit of growth.

Asexual reproduction of my new variety by cuttings through a series of annual propagations at Oakland and Hayward, Calif., shows that all characteristics of the variety come true to form through succeeding propagations. The accompanying photographs illustrate the primary characteristics of my new variety as nearly true as is reasonably possible to make them with presently available techniques. The color references cited are those of the Horticultural Colour Charts of the Royal Horticultural Society.

The following botanical description is based upon observation of own rooted plants produced and grown under average conditions in greenhouses at Oakland and Hayward, Calif. from 1950 to 1968.

The plant is upright to somewhat spreading at maturity, vigorous, branching from the base, heavily branched and profusely flowering, so much so as to almost hide the foliage when in full bloom. Mature height 30" to 36", spreading to 40–44". Flowering time substantially later than most Belgian-Indicas normally peaking the second or third week in May. Duration of peak bloom 3–4 weeks.

The branches are stout, somewhat arching, gray to brown, coarsely striated with the older bark gray, and tending to exfoliate. Five year stems are ⅜–⅝ inch in diameter. The young shoots are slender, but stiff, light green, turning brown at maturity, and clothed witih moderate to dense strigae which are subhyaline, tan to light brown, long lanceolate, ten tlmes as long as broad or more. The internodes are about ½" long.

The foliage is of essentially one size class, obovate, petiolate, margin entire and ciliate. The lamina is narrowly decurrent to the base. Petiole and midrib strigose. The strigae are longer and more conspicuous than those of the stem, light chestnut-brown, hyaline on the margins and at the tip, otherwise opaque. Leaves about ⅞–1⅛" long, by ⅜–¾" wide, tip of the leaf accuminate, mucronate. Lamina about 1" long, petiole about ⅛" long. Color of the leaves dark Spinach Green (HCC 0960) and somewhat shiny above, light Willow Green (HCC 000862/1) and glaucous below. Upper surface sparsely ciliate, lower surface very sparsely ciliate.

The flowers are solitary at the ends of branches, rarely more than one. The buds are small about ¼" long by ⅙" wide, narrowly lanceolate, pointed. The flower is broadly funnel-shaped, 1½ inches deep by 2½ inches wide, essentially pure white, but with some yellow within and without the tube. The flower is zygomorphic with the two ventral corolla lobes larger and more reflexed than the three dorsal lobes.

The peduncle is stout, moderately strigose, light green.

The strigae are light chestnut and essentially the same as those of the petiole. The peduncle is about 3/32 inch in diameter and about 7/32 inch long. The calyx is small, about 5/16 inch across, and light green. The calyx lobes are five, small, about 3/32 inch wire by 1/16 inch long, ovate, entire. The margin is long ciliate. The cilia are up to 3/32 inch long and more abundant at the tip. The tip is rounded. The outer surface of the calyx is sparsely pubescent and the inner surface is glaabrous.

The corolla is about 2½ inches broad by ⅜ inch deep. The ventral lobes are circular in outline with entire, but undulate margins and subauriculate at the base, 1⅙–1¼ inches in diameter. The dorsal lobes are ovate-cordate, smaller than the ventral, about 1⅛ inch wide or less and ⅞–1 inch long. The tube of the corolla is ½ to ⅝" long and about 1 inch across. There are faint yellow splotches at the base of the mid dorsal lobe.

The stamens are modified into a corolliform organ wiith 8–12 lobes fused into a tube at the base, white as in the corolla, the tube is short about ⅜ inch long by 1 inch wide at the throat. The tube is somewhat plicated. The lobes of the modified androecium are of various sizes, but most are long, large, and folded and ruffled to give the flower a very double effect. The larger lobes are about the same size and shape as the dorsal corolla lobes. The smaller are from ⅙–1¼ inches long. There are usually no normal stamens, but anther tissue occurs on some of the staminodia, and pollen in limited amounts is produced. The usual condition is for pollen bearing thecae to occur on some of the medium sized lobes. These pollen bearing lobes are variously ornate with secondary lobes.

The pistil is generally normal, though occasionally somewhat modified, about 1⅜ inches long. The ovary is green, densely pubescent about 3/16 inch long by ⅙ inch wide, ovate. The trichomes are hyaline, silvery white, almost wooly giving the ovary the appearance of being white when viewed from the side. The style is ivory white, and when young may have yellow or pink tints. It is long and slender about 1¼ inches long by 1/32 inch in diameter, only slightly sigmoid and with the stigma presented at about 30 degrees from the vertical. The stigma is greenish yellow, glistening, capitate and inconspicuously lobed.

Having thus disclosed my invention, I claim:

1. A new and distinct variety of azalea plant of the Belgian-Indica type substantially as herein shown and described primarily characterized by: a normal flowering date substantially later than most Belgian-Indicas reaching peak bloom about the second or third week in May, by its nearly pure white, fully double blooms; by its profuse bloom; by its long blooming period and exceptional rentention of blooms and by its vigor, ease of propagation an dcompact habit of growth.

No references cited.

ROBERT E. BAGWILL, Primary Examiner